US006921528B2

(12) United States Patent
Edwards et al.

(10) Patent No.: US 6,921,528 B2
(45) Date of Patent: **\*Jul. 26, 2005**

(54) HIGHLY EFFICIENT DELIVERY OF A LARGE THERAPEUTIC MASS AEROSOL

(75) Inventors: David A. Edwards, Boston, MA (US); Richard P. Batvcky, Auburndale, MA (US); Lloyd Johnston, Belmont, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 10 days.

This patent is subject to a terminal disclaimer.

(21) Appl. No.: 10/681,416

(22) Filed: Oct. 8, 2003

(65) Prior Publication Data

US 2004/0076589 A1 Apr. 22, 2004

Related U.S. Application Data

(62) Division of application No. 09/591,307, filed on Jun. 9, 2000, now Pat. No. 6,858,199.

(51) Int. Cl.⁷ .............................. A61K 9/12; A61K 9/14; A61K 9/72
(52) U.S. Cl. ........................... 424/45; 424/46; 424/489; 424/499; 424/434; 514/2; 514/3
(58) Field of Search .......................... 424/45, 46, 434, 424/489, 499; 514/2, 3, 12, 13

(56) References Cited

U.S. PATENT DOCUMENTS

| | | | |
|---|---|---|---|
| 4,069,819 A | 1/1978 | Valentini et al. | |
| 4,995,385 A | 2/1991 | Valentini et al. | |
| 5,260,306 A | 11/1993 | Boardman et al. | |
| 5,304,125 A | 4/1994 | Leith | |
| 5,306,483 A | 4/1994 | Mautone | |
| 5,506,203 A | 4/1996 | Bäckström et al. | |
| 5,518,998 A | 5/1996 | Bäckström et al. | |
| 5,641,510 A | 6/1997 | Clark et al. | |
| 5,642,728 A | 7/1997 | Andersson et al. | |
| 5,795,594 A | 8/1998 | York et al. | |
| 5,830,853 A | 11/1998 | Bäckström et al. | |
| 5,851,453 A | 12/1998 | Hanna et al. | |
| 5,855,913 A | 1/1999 | Hanes et al. | |
| 5,874,064 A | 2/1999 | Edwards et al. | |
| 5,985,309 A | 11/1999 | Edwards et al. | |
| 5,993,805 A | 11/1999 | Sutton et al. | |
| 5,997,848 A | 12/1999 | Patton et al. | |
| 6,019,968 A | 2/2000 | Platz et al. | |
| 6,051,256 A | 4/2000 | Platz et al. | |
| 6,063,138 A | 5/2000 | Hanna et al. | |
| 6,136,295 A | 10/2000 | Edwards et al. | |
| 6,165,463 A | 12/2000 | Platz et al. | |
| RE37,053 E | 2/2001 | Hanes et al. | |
| 6,254,854 B1 | 7/2001 | Edwards et al. | |
| 6,284,282 B1 | 9/2001 | Maa et al. | |
| 6,372,258 B1 | 4/2002 | Platz et al. | |
| 6,399,102 B1 | 6/2002 | Edwards et al. | |
| 6,423,344 B1 | 7/2002 | Platz et al. | |
| 6,436,443 B2 | 8/2002 | Edwards et al. | |
| 6,447,752 B2 | 9/2002 | Edwards et al. | |
| 6,447,753 B2 | 9/2002 | Edwards et al. | |
| 6,503,480 B1 | 1/2003 | Edwards et al. | |
| 6,652,837 B1 | 11/2003 | Edwards et al. | |

FOREIGN PATENT DOCUMENTS

| | | |
|---|---|---|
| WO | WO 95/00127 | 1/1995 |
| WO | WO 96/09814 | 4/1996 |
| WO | WO 96/32096 | 10/1996 |
| WO | WO 96/32149 | 10/1996 |
| WO | WO 97/44013 | 11/1997 |
| WO | WO 98/16205 | 4/1998 |
| WO | WO 98/17257 | 4/1998 |
| WO | WO 98/31346 | 7/1998 |
| WO | WO 99/16419 | 4/1999 |
| WO | WO 99/66903 | 12/1999 |
| WO | WO 00/10541 | 3/2000 |
| WO | WO 00/33811 | 6/2000 |
| WO | WO 01/13893 A2 | 3/2001 |
| WO | WO 01/51030 A1 | 7/2001 |

OTHER PUBLICATIONS

Hanes, J., et al., "Porous Dry–Powder PLGA Microspheres Coated with Lung Surfactant Forsystemic Insulin Delivery Via the Lung," *Controlled Release Soc.*, 24:57–58.

Edwards, David A., et al. "Large Porous Aerosols for Pulmonary Drug Delivery," *Proc. Int. Symp. Controlled Release Bioact. Mater.*, 24:67–68 (1997).

Anderson, S.D. et al., "A New Method for Bronchial–Provocation Testing in Asthmatic Subjects Using a Dry Powder of Mannitol," *Am. J. Respir. Crit. Care Med.* 156:758–765 (1997).

Anderson, S.D. et al., "The Effect of Inhaling a Dry Powder of Sodium Chloride on the Airways of Asthmatic Subjects," *Eur. Respir. J.* 10:2465–2476 (1997).

Ben–Jebria, A. et al., "Large Porous Particles for Sustained Protection from Carbachol–Induced Bronchoconstriction in Guinea Pigs," *Pharm. Res.* 16(4):555–561 (1999).

(Continued)

*Primary Examiner*—Gary Kunz
*Assistant Examiner*—Mina Haghighatian
(74) *Attorney, Agent, or Firm*—Elmore, Craig & Vanstone, P.C.; Anne I. Craig; Carolyn S. Elmore (57) ABSTRACT

A method for delivering a therapeutic dose of a bioactive agent to the pulmonary system, in a single, breath-activated step, comprises administering from a receptacle enclosing a mass of particles, to a subject's respiratory tract, particles which have a tap density of less than 0.4 g/cm³ and deliver at least about 50% of the mass of particles. Another method of delivering a therapeutic dose of a bioactive agent to the pulmonary system, in a single breath, includes administering from a receptacle enclosing a mass of particles, to a subject's respiratory tract, particles which have a tap density of at least 0.4 g/cm³ and deliver at least about 10 milligrams of the bioactive agent. The receptacle can have a volume of at least 0.37 cm³.

19 Claims, 6 Drawing Sheets

OTHER PUBLICATIONS

Cipolla, D. et al., "Bolus Administration of INS365: Studying the Feasibility of Delivering High Dose Drugs Using the AERx® Pulmonary Delivery System," *Respiratory Drug Delivery, VII*:231–239 (2000).

Edwards, D.A., "The Macrotransport of Aerosol Particles in the Lung: Aerosol Deposition Phenomena," *J. Aerosol Sci.,* 26(2):293–317 (1995).

Edwards, D.A. et al., "Large Porous Particles for Pulmonary Drug Delivery," *Science* 276:1868–71 (1997).

Huang, C–H. et al., "Calorimetric and Molecular Mechanics Studies of the Thermotropic Phase Behavior of Membrane Phospholipids," *Biochim. Biophys. Acta., 1422*:273–307 (1999).

Pritchard, J.N. et al., "Use of In Vitro Particle Size Data to Predict Deposition and Effects of Inhaled Drugs," *International Conference on Aerosol Therapy.* Italy, (Dec. 2–5, 1998).

Scheuch, G. et al., "Measuring in vivo deposition of large porous particles," *Journal of Aerosol Medicine 12(2)*:127–138 (1999).

Wang, J. et al., "Inhalation of Estradiol for Sustained Systemic Delivery," *Journal of Aerosol Medicine, 12(1)*:27–36 (1999).

Wolff, R.K., "Safety of Inhaled Proteins for Therapeutic Use," *Journal of Aerosol Medicine, 11(4)*:197–219 (1998).

HIGHLY EFFICIENT DELIVERY OF A LARGE THERAPEUTIC MASS AEROSOL

RELATED APPLICATIONS

This application is a divisional application of U.S. application Ser. No. 09/591,307, filed Jun. 9, 2000 now U.S. Pat. No. 6,858,199. The entire teachings of the above application(s) are incorporated herein by reference.

BACKGROUND OF THE INVENTION

Aerosols for the delivery of therapeutic agents to the respiratory tract have been described, for example, Adjei, A. and Garren, J. *Pharm. Res.,* 7: 565–569 (1990); and Zanen, P. and Lamm, J.-W. J. *Int. J. Pharm.,* 114: 111–115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems,* 6: 273–313 (1990). The deep lung, or alveoli, are the primary target of inhaled therapeutic aerosols for systemic drug delivery.

Inhaled aerosols have been used for the treatment of local lung disorders including asthma and cystic fibrosis (Anderson, *Am. Rev. Respir. Dis.,* 140: 1317–1324 (1989)) and have potential for the systemic delivery of peptides and proteins as well (Patton and Platz, *Advanced Drug Delivery Reviews,* 8: 179–196 (1992)).

Relatively high bioavailability of many molecules, including macromolecules, can be achieved via inhalation. Wall, D. A., *Drug Delivery,* 2: 1–20 (1995); Patton, J. and Platz, R., *Adv. Drug Del. Rev.,* 8: 179–196 (1992); and Byron, P., *Adv. Drug. Del. Rev.,* 5: 107–132 (1990). As a result, several aerosol formulations of therapeutic drugs are in use or are being tested for delivery to the lung. Patton, J. S., et al., *J. Controlled Release,* 28: 79–85 (1994); Damms, B. and Bains, W., *Nature Biotechnology* (1996); Niven, R. W., et al., *Pharm. Res.,* 12(9): 1343–1349 (1995); and Kobayashi, S., et al., *Pharm. Res.,* 13(1): 80–83 (1996).

However, pulmonary drug delivery strategies present many difficulties, in particular for the delivery of macromolecules; these include protein denaturation during aerosolization, excessive loss of inhaled drug in the oropharyngeal cavity (often exceeding 80%), poor control over the site of deposition, lack of reproducibility of therapeutic results owing to variations in breathing patterns, the frequent too-rapid absorption of drug potentially resulting in local toxic effects, and phagocytosis by lung macrophages.

In addition, many of the devices currently available for inhalation therapy are associated with drug losses. Considerable attention has been devoted to the design of therapeutic aerosol inhalers to improve the efficiency of inhalation therapies. Timsina et. al., *Int. J. Pharm.,* 101: 1–13 (1995); and Tansey, I. P., *Spray Technol. Market,* 4: 26–29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., *J. Aerosol Sci.,* 27: 769–783 (1996).

Dry powder formulations (DPF's) are gaining increased interest as aerosol formulations for pulmonary delivery. Damms, B. and W. Bains, *Nature Biotechnology* (1996); Kobayashi, S., et al., *Pharm. Res.,* 13(1): 80–83 (1996); and Timsina, M., et al., *Int. J. Pharm.,* 101: 1–13 (1994). Dry powder aerosols for inhalation therapy are generally produced with mean geometric diameters primarily in the range of less than 5 μm. Ganderton, D., *J. Biopharmaceutical Sciences,* 3: 101–105 (1992); and Gonda, I. "Physico-Chemical Principles in Aerosol Delivery," in *Topics in Pharmaceutical Sciences* 1991, Crommelin, D. J. and K. K. Midha, Eds., Medpharm Scientific Publishers, Stuttgart, pp. 95–115, 1992. Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.,* 27: 769–783 (1996).

Among the disadvantages of DPF's is that powders of fine particulates usually have poor flowability and aerosolization properties, leading to relatively low respirable fractions of aerosol, which are the fractions of inhaled aerosol that deposit in the lungs, escaping deposition in the mouth and throat. Gonda, I., in *Topics in Pharmaceutical Sciences* 1991, D. Crommelin and K. Midha, Editors, Stuttgart: Medpharm Scientific Publishers, 95–117 (1992). Poor flowability and aerosolization properties are typically caused by particulate aggregation, due to particle-particle interactions, such as hydrophobic, electrostatic, and capillary interactions. Some improvements in DPF's have been made for instance. Dry powder formulations ("DPFs") with large particle size have improved flowability characteristics, such as less aggregation (Edwards, et al., *Science* 276:1868–1871 (1997)), easier aerosolization, and potentially less phagocytosis. Rudt, S. and R. H. Muller, *J. Controlled Release,* 22: 263–272 (1992); Tabata, Y. and Y. Ikada, *J. Biomed. Mater. Res.,* 22: 837–858 (1988). An effective dry-powder inhalation therapy for both short and long term release of therapeutics, either for local or systemic delivery, requires a method to deliver DPF to the lungs efficiently, and at therapeutic levels, without requiring excessive energy input.

Nebulizers, such as described by Cipolla et al., Respiratory Drug Delivery VII, Biological, Pharmaceutical, Clinical and Regulatory Issues Relating to Optimized Drug Delivery by Aerosol, Conference held May 14–18, 2000, Palm Springs, Fla., the contents of which are incorporated herein by reference in their entirety, also are employed in pulmonary delivery.

Inhalation devices which can be employed to deliver dry powder formulations to the lungs include non-breath-activated or "multistep" devices. One such device is described in U.S. Pat. No. 5,997,848 issued to Patton et al. on Dec. 7, 1999, the entire teachings of which are incorporated herein by reference. In these devices, the drug formulation is first dispersed by energy independent of a patient's breath, then inhaled.

Inhalation devices that utilize a "single, breath activated-step" disperse the powder and inhale it at the same time, i.e., in a single step, for example, a simple dry powder inhaler. (U.S. Pat. Nos. 4,995,385 and 4,069,819). Other examples of inhalers include the Spinhaler® (Fisons, Loughborough, U.K.), Rotahaler® (Glaxo-Wellcome, Research Triangle Park, N.C.).

In comparison to "single-step" inhalers, existing "multi-step inhalers" are more complex to operate and tend to be more costly since extra energy is needed to deliver a drug to the lungs. This energy increases with increasing drug mass. On the other hand, "high efficiency" of drug delivery to the respiratory tract, meaning about 50% of the drug mass initially contained in a drug receptacle, (i.e., the "nominal dose"), is typically only achieved with breath-activated, multi-step inhaler systems. Therefore, patients have until now needed to make a choice between cost/complexity and efficiency of drug delivery. The reason for this trade-off is that existing inhalation methodologies and devices are associated with inherent formulation inefficiencies and/or inherent device design limitations. Such inefficiencies result in unwanted drug losses and elevated overall cost of treatment. In addition, and often as a consequence, existing inhalation devices and methodologies can often fail to deliver to the lung a sufficient (i.e., therapeutic) mass of drug in a single breath. Currently, the amount of drug that can be delivered to the lung in a single breath, via liquid or dry powder inhalers generally does not exceed 5 mg (Cipolla, et al., *Resp. Drug Delivery VII* 2000:231–239 (2000)).

Therefore a need exists for delivering to the pulmonary system a bioactive agent wherein at least about 50% of the nominal dose of the bioactive agent is delivered to the pulmonary system via a single step inhalation system. A need also exists for delivery of a relatively large mass of a bioactive agent, such as, for example, a therapeutic, prophylactic or diagnostic agent. A need further exists for methods of delivering to the pulmonary system, in a single step, from a simple breath-activated device, a single, high dose of a bioactive agent.

SUMMARY OF THE INVENTION

The invention is related to methods of delivery of a bioactive agent to the pulmonary system.

In one embodiment of the invention, a method of delivering a therapeutic dose of a bioactive agent to the pulmonary system, in a single, breath-activated step, includes administering particles, from a receptacle having, holding, containing or enclosing a mass of particles, to the respiratory tract of a subject, wherein at least 50% of the mass of particles is delivered. The particles have a tap density of less than about 0.4 g/cm$^3$. In another embodiment of the invention, a method of delivering a therapeutic dose of a bioactive agent to the pulmonary system in a single breath, includes administering particles from a receptacle. The particles have a tap density of at least about 0.4 g/cm$^3$ and deliver to the pulmonary system at least about 5 milligrams, preferably at least about 10 milligrams of a bioactive agent. In a preferred embodiment, the particles deliver at least about 15 milligrams of bioactive agent. In another preferred embodiment, the particles deliver at least about 20 milligrams of bioactive agent. In still another preferred embodiment, the particles deliver at least about 25 milligrams of bioactive agent. In a further preferred embodiment, the particles deliver at least about 30 milligrams of bioactive agent in which the receptacle has a volume of at least 0.48 cm$^3$. Higher amounts can also be delivered, for example the particles can deliver at least about 35, 40 or 50 milligrams of bioactive agent. In other embodiments, the receptacle can have a volume of 0.95 cm$^3$.

In one embodiment the receptacle has a volume of at least about 0.37 cm$^3$ and can have a design suitable for use in a dry powder inhaler. Larger receptacles having a volume of at least about 0.48 cm$^3$, 0.67 cm$^3$ or 0.95 cm$^3$ also can be employed.

In a preferred embodiment, the energy holding the particles of the dry powder in an aggregated state is such that a patient's breath, over a reasonable physiological range of inhalation flow rates is sufficient to deaggregate the powder contained in the receptacle into respirable particles. The deaggregated particles can penetrate via the patient's breath into and deposit in the airways and/or deep lung with high efficiency.

In one embodiment of the invention, the particles have a tap density of less than about 0.4 g/cm$^3$, preferably around 0.1 g/cm$^3$ or less. In another embodiment, the particles have a mass median geometric diameter (MMGD) larger than 5 μm, preferably around about 10 μm or larger. In yet another embodiment, the particles have a mass median aerodynamic diameter (MMAD) ranging from about 1 μm to about 5 μm.

The invention has numerous advantages. For example, a large single dose of a therapeutic, prophylactic or diagnostic agent can be administered to the pulmonary system via a DPI with high efficiency. The invention employs a simple, cost effective device for pulmonary delivery which increases efficiency and minimizes wasted drug. Since dosage frequency can be reduced by the delivery method of the invention, patient compliance to treatment or prophylaxis protocols is expected to improve. Pulmonary delivery advantageously can eliminate the need for injection. For example, the requirement for daily insulin injections can be avoided.

DETAILED DESCRIPTION OF THE INVENTION

The features and other details of the invention, either as steps of the invention or as combination of parts of the 
invention, will now be more particularly described with reference to the accompanying drawings and pointed out in the claims. It will be understood that the particular embodiments of the invention are shown by way of illustration and not as limitations of the invention. The principle feature of this invention may be employed in various embodiments without departing from the scope of the invention.

The invention is related to methods of delivery to the pulmonary system of a subject particles comprising a bioactive agent.

The methods of the invention relate to administering to the respiratory tract of a subject particles enclosed in a receptacle. As used herein, the term "receptacle" includes but is not limited to, for example, a capsule, blister, film covered container well, chamber and other suitable means of storing a powder in an inhalation device known to those skilled in the art.

In a preferred embodiment, the receptacle is used in a dry powder inhaler. Examples of dry powder inhalers that can be employed in the methods of the invention include but are not limited to the inhalers disclosed is U.S. Pat. Nos. 4,995,385 and 4,069,819, the Spinhaler® (Fisons, Loughborough, U.K.), Rotahaler® (Glaxo-Wellcome, Research Triangle Technology Park, North Carolina), FlowCaps® (Hovione, Loures, Portugal), Inhalator® (Boehringer-Ingelheim, Germany), and the Aerolizer® (Novartis, Switzerland), the Diskhaler (Glaxo-Wellcome, RTP, NC) and others known to those skilled in the art.

In one embodiment, the volume of the receptacle is at least about 0.37 $cm^3$. In another embodiment, the volume of the receptacle is at least about 0.48 $cm^3$. In yet another embodiment, are receptacles having a volume of at least about 0.67 $cm^3$ or 0.95 $cm^3$. In one embodiment of the invention, the receptacle is a capsule designated with a capsule size 2, 1, 0, 00 or 000. Suitable capsules can be obtained, for example, from Shionogi (Rockville, Md.). Blisters can be obtained, for example, from Hueck Foils, (Wall, N.J.)

The receptacle encloses or stores particles, also referred to herein as powders. The receptacle is filled with particles, as known in the art. For example, vacuum filling or tamping technologies may be used. Generally, filling the receptacle with powder can be carried out by methods known in the art. In one embodiment of the invention, the article or powder enclosed or stored in the receptacle have a mass of at least about 5 milligrams. Preferably, the mass of the particles stored or enclosed in the receptacle is at least about 10 milligrams.

Particles, especially highly dispersible particles as defined herein, stored in the receptacle comprise a bioactive agent. Examples of bioactive agents include therapeutic, prophylactic or diagnostic agents. Specific examples of bioactive agents include drugs, pharmaceutical formulations, vitamins, pharmaceutical adjuvants, proteins, peptides, polypeptides, hormones, amino acids, nucleic acids, vaccine formulations, inactivated viruses, lung surfactants and any combinations thereof. Other examples include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies, such as, for example, monoclonal antibodies, e.g., palivizumab (Medimmune, Gaithersberg, Md.). In some instances, the proteins may be antibodies or antigens which otherwise would have to be administered by injection to elicit an appropriate response. Compounds with a wide range of molecular weight can be encapsulated, for example, between 100 and 500,000 Daltons. Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

The particles, especially the highly dispersible particles described herein, may include a therapeutic or prophylactic agent suitable for systemic treatment. Alternatively, the particles can include a therapeutic or prophylactic agent for local delivery within the lung, such as, for example, agents for the treatment of asthma, emphysema, or cystic fibrosis, or for systemic treatment. For example, genes for the treatment of diseases such as cystic fibrosis can be administered, as can beta agonists for asthma. Other specific therapeutic agents include, but are not limited to, human growth hormone, interleukins, insulin, calcitonin, leutinizing hormone releasing hormone gonadotropin-releasing hormone ("LHRH") and analogs thereof (e.g. leoprolide), granulocyte colony-stimulating factor ("G-CSF"), parathyroid hormone-related peptide, somatostatin, testosterone, progesterone, estradiol, nicotine, fentanyl, norethisterone, clonidine, scopolomine, salicylate, cromolyn sodium, salmeterol, formeterol, ipratropium bromide, albuterol, fluticasone and valium. Other suitable therapeutic or prophylatic agents include, but are not limited to those listed in U.S. Pat. No. 5,875,776, the entire teachings of which are incorporated herein by reference. Those therapeutic agents which are charged, such as most of the proteins, including insulin, can be administered as a complex between the charged therapeutic agent and a molecule of opposite charge. Preferably, the molecule of opposite charge is a charged lipid or an oppositely charged protein. The particles can incorporate substances such as lipids which allow for the sustained release of small and large molecules. Addition of these complexes or substances is applicable to particles of any size and shape, and is especially useful for altering the rate of release of therapeutic agents from inhaled particles.

Any of a variety of diagnostic agents can be incorporated within the highly dispersible particles, which can locally or systemically deliver the incorporated agents following administration to a patient. Particles incorporating diagnostic agents can be detected using standard techniques available in the art and commercially available equipment.

Any biocompatible or pharmacologically acceptable gas, for example, can be incorporated into the particles or trapped in the pores of the particles using technology known to those skilled in the art. The term gas refers to any compound which is a gas or capable of forming a gas at the temperature at which imaging is being performed. In one embodiment, retention of gas in the particles is improved by forming a gas-impermeable barrier around the particles. Such barriers are well known to those of skill in the art.

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Bioactive agents also include targeting molecules which can be attached to the particles via reactive functional groups on the particles. For example, targeting molecules can be attached to the amino acid groups of functionalized polyester graft copolymer particles, such as poly(lactic acid-co-lysine) (PLAL-Lys) particles. Targeting molecules permit binding interaction of the particle with specific receptor sites, such as those within the lungs. The particles can be targeted by attachment of ligands which specifically or non-specifically bind to particular targets. Exemplary targeting molecules include antibodies and fragments thereof including the variable regions, lectins, and hormones or other organic molecules capable of specific binding, for example, to receptors on the surfaces of the target cells.

Bioactive agents can also include surfactants such as surfactants endogenous to the lung; both naturally occurring and synthetic lung surfactants are included.

In one embodiment of the invention, the receptacle encloses a mass of particles, especially a mass of highly dispersible particles described herein. The mass of particles comprises a nominal dose of the bioactive agent. As used herein, the phrase "nominal dose" means the total mass of bioactive agent which is present in the mass of particles in the receptacle and represents the maximum amount of bioactive agent available for administration in a single breath.

Particles stored or enclosed in the receptacles are administered to the respiratory tract of a subject. As used herein, the terms "administration" or "administering" of particles refer to introducing particles to the respiratory tract of a subject (through the nose and/or through the mouth).

In one embodiment of the invention, the particles are administered in a single, breath-activated step. As used herein, the phrases "breath-activated" and "breath-actuated" are used interchangeably. As used herein, "a single, breath-activated step" means that particles are dispersed and inhaled in one step. For example, in single, breath-activated inhalation devices, the energy of the subject's inhalation both disperses particles and draws them into the oral or nasopharyngeal cavity. Suitable inhalers which are single, breath-actuated inhalers that can be employed in the methods of the invention include but are not limited to simple, dry powder inhalers disclosed in U.S. Pat. Nos. 4,995,385 and 4,069,819, the Spinhaler® (Fisons, Loughborough, U.K.), Rotahaler® (Glaxo-Wellcome, Research Triangle Technology Park, North Carolina), FlowCaps® (Hovione, Loures, Portugal), Inhalator® (Boehringer-Ingelheim, Germany), and the Aerolizer® (Novartis, Switzerland), the Diskhaler (Glaxo-Wellcome, RTP, NC) and others, such as known to those skilled in the art.

"Single breath" administration can include single, breath-activated administration, but also administration during which the particles or powders are first dispersed, followed by the inhalation or inspiration of the dispersed particles. In the latter mode of administration, additional energy than the energy supplied by the subject's inhalation disperses the particles. An example of a single breath inhaler which employs energy other than the energy generated by the patient's inhalation includes but is not limited to the device described in U.S. Pat. No. 5,997,848 issued to Patton et al. on Dec. 7, 1999, the entire teachings of which are incorporated herein by reference.

In a preferred embodiment, the receptacle enclosing the particles is emptied in a single, breath-activated step. In another preferred embodiment, the receptacle enclosing the particles is emptied in a single inhalation. As used herein, the term "emptied" means that at least 50% of the particle mass enclosed in the receptacle is emitted from the inhaler during administration of the particles to a subject's respiratory system.

In a preferred embodiment of the invention, the particles administered are highly dispersible. As used herein, the phrase "highly dispersible" particles or powders refers to particles or powders which can be dispersed by a RODOS dry powder disperser (or equivalent technique) such that at about 1 Bar, particles of the dry powder emit from the RODOS orifice with geometric diameters, as measured by a HELOS or other laser diffraction system, that are less than about 1.5 times the geometric particle size as measured at 4 Bar. Highly dispersible powders have a low tendency to agglomerate, aggregate or clump together and/or, if agglomerated, aggregated or clumped together, are easily dispersed or de-agglomerated as they emit from an inhaler and are breathed in by the subject. Typically, the highly dispersible particles suitable in the methods of the invention display very low aggregation compared to standard micronized powders which have similar aerodynamic diameters and which are suitable for delivery to the pulmonary system. Properties that enhance dispersibility include, for example, particle charge, surface roughness, surface chemistry and relatively large geometric diameters. In one embodiment, because the attractive forces between particles of a powder varies (for constant powder mass) inversely with the square of the geometric diameter and the shear force seen by a particle increases with the square of the geometric diameter, the ease of dispersibility of a powder is on the order of the inverse of the geometric diameter raised to the fourth power. The increased particle size diminishes interparticle adhesion forces. (Visser, J., *Powder Technology*, 58: 1–10 (1989)). Thus, large particle size, all other things equivalent, increases efficiency of aerosolization to the lungs for particles of low envelope mass density. Increased surface irregularities, and roughness also can enhance particle dispersibility. Surface roughness can be expressed, for example by rugosity.

The particles preferably are biodegradable and biocompatible, and optionally are capable of biodegrading at a controlled rate for delivery of a therapeutic, prophylactic, or diagnostic agent. In addition to the bioactive agent, the particles can further include a variety of materials. Both inorganic and organic materials can be used. For example, ceramics may be used. Polymeric as well as non-polymeric materials, such as fatty acids, may be used to form aerodynamically light particles. Other suitable materials include, but are not limited to, amino acids, gelatin, polyethylene glycol, trehalose, lactose, and dextran. Preferred particle compositions are further described below.

In one embodiment of the invention, particles administered to a subject's respiratory tract have a tap density of less than about 0.4 g/cm$^3$. Particles having a tap density of less than about 0.4 g/cm$^3$ are referred to herein as "aerodynamically light". In a preferred embodiment, the particles have a tap density of near to or less than about 0.1 g/cm$^3$. Tap density is a measure of the envelope mass density charac- 
terizing a particle. The envelope mass density of a particle of a statistically isotropic shape is defined as the mass of the particle divided by the minimum sphere envelope volume within which it can be enclosed. Features which can contribute to low tap density include irregular surface texture and hollow or porous structure.

Tap density can be measured by using instruments known to those skilled in the art such as the Dual Platform Microprocessor Controlled Tap Density Tester (Vankel, N.C.). Tap density is a standard measure of the envelope mass density. Tap density can be determined using the method of USP Bulk Density and Tapped Density, United States Pharmacopia convention, Rockville, Md., $10^{th}$ Supplement, 4950–4951, 1999.

In another embodiment, the particles have a mass median geometric diameter (MMGD) greater than about 5 μm and preferably near to or greater than about 10 μm. In one embodiment, the particles have a MMGD greater than about 5 μm and ranging to about 30 μm. In another embodiment, the particles have a MMGD ranging from about 10 μm to about 30 μm.

The mass MMGD of the particles can be measured using an electrical zone sensing instrument such as Coulter Multisizer IIe (Coulter Electronics, Luton, Beds, England) or a laser diffraction instrument (for example Helos, Sympatec, Inc., Princeton, N.J.). The diameter of particles in a sample will range depending upon factors such as particle composition and methods of synthesis. The distribution of size of particles in a sample can be selected to permit optimal deposition within targeted sites within the respiratory tract.

The aerodynamically light particles suitable for use in the instant invention may be fabricated or separated, for example by filtration or centrifugation, to provide a particle sample with a preselected size distribution. For example, greater than 30%, 50%, 70%, or 80% of the particles in a sample can have a diameter within a selected range of at least 5 μm. The selected range within which a certain percentage of the particles must fall may be for example, between about 5 and 30 μm, or optionally between 5 and 15 μm. In one preferred embodiment, at least a portion of the particles have a diameter between about 9 and 11 μm. Optionally, the particle sample also can be fabricated wherein at least 90%, or optionally 95% or 99%, have a diameter within the selected range. The presence of the higher proportion of the aerodynamically light, larger diameter (at least about 5 μm) particles in the particle sample enhances the delivery of therapeutic prophylactic, or diagnostic agents incorporated therein to the deep lung.

In one embodiment, in the particle sample, the interquartile range may be 2 μm, with a mean diameter for example, between about 7.5 and 13.5 μm. Thus, for example, between at least 30% and 40% of the particles may have diameters within the selected range. Preferably, the said percentages of particles have diameters within a 1 μm range, for example, between 6.0 and 7.0 μm, 10.0 and 11.0 μm or 13.0 and 14.0 μm.

In a further embodiment, the particles have an aerodynamic diameter ranging from about 1 μm to about 5 μm. The aerodynamic diameter, $d_{aer}$, can be calculated from the equation:

$$d_{aer}=d_g\sqrt{\rho_{tap}}$$

where $d_g$ is the geometric diameter, for example the MMGD and ρ is the powder density. Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI).

In one embodiment of the invention, at least 50% of the mass of the particles stored in the receptacle are delivered to a subject's respiratory tract in a single, breath-activated step. Preferably, at least 55% of the mass of particles is delivered.

In another embodiment of the invention, at least 5 milligrams and preferably at least 10 milligrams of bioactive agent is delivered by administering, in a single breath, to a subject's respiratory tract particles enclosed in the receptacle. Amounts of at least 15, preferably of at least 20 and more preferably of at least 25, 30, 35, 40 and 50 milligrams can be delivered. In a preferred embodiment, amounts of at least 35 milligrams are delivered. In another preferred embodiment, amounts of at least 50 milligrams are delivered.

Particles administered to the respiratory tract of the subject are delivered to the pulmonary system. Particles suitable for use in the methods of the invention can travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In one embodiment of the invention, most of the mass of particles deposit in the deep lung. In another embodiment of the invention, delivery is primarily to the central airways. In other embodiments, delivery is to the upper airways.

The particles suitable for use in the instant invention may be fabricated with the appropriate material, surface roughness, diameter and tap density for localized delivery to selected regions of the respiratory tract such as the deep lung, central or upper airways. For example, higher density or larger particles may be used for upper airway delivery, or a mixture of different sized particles in a sample, provided with the same or different therapeutic agent may be administered to target different regions of the lung in one administration. Particles with degradation and release times ranging from seconds to months can be designed and fabricated, based on factors such as the particle material.

Delivery to the pulmonary system of particles in a single, breath-actuated step is enhanced by employing particles which are dispersed at relatively low energies, such as, for example, at energies typically supplied by a subject's inhalation. Such energies are referred to herein as "low". As used herein, "low energy administration" refers to administration wherein the energy applied to disperse and inhale the particles is in the range typically supplied by a subject during inhaling.

In one embodiment of the invention, highly dispersible particles administered comprise a bioactive agent and a biocompatible, and preferably biodegradable polymer, copolymer, or blend. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)-hexane anhydride] (PCPH) may be used. Biodegradable polyanhydrides are described in U.S. Pat. No. 4,857,311. Bulk eroding polymers such as those based on polyesters including poly(hydroxy acids) also can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(D,L-lactic-co-glycolic acid) ("PLGA") which incorporate a surfactant such as dipalmitoyl phosphatidylcholine (DPPC).

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

Highly dispersible particles can be formed from functionalized polyester graft copolymers, as described in Hrkach et al., *Macromolecules,* 28: 4736–4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications,* ACS Symposium Series No. 627, Raphael M. Ottenbrite et al., Eds., American Chemical Society, Chapter 8, pp. 93–101, 1996.

In a preferred embodiment of the invention, highly dispersible particles including a bioactive agent and a phospholipid are administered. Examples of suitable phospholipids include, among others, phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combination thereof. Other phospholipids are known to those skilled in the art. In a preferred embodiment, the phospholipids are endogenous to the lung.

The phospholipid, can be present in the particles in an amount ranging from about 0 to about 90 weight %. More commonly it can be present in the particles in an amount ranging from about 10 to about 60 weight %.

In another embodiment of the invention, the phospholipids or combinations thereof are selected to impart controlled release properties to the highly dispersible particles. The phase transition temperature of a specific phospholipid can be below, around or above the physiological body temperature of a patient. Preferred phase transition temperatures range from 30° C. to 50° C., (e.g., within ±10 degrees of the normal body temperature of patient). By selecting phospholipids or combinations of phospholipids according to their phase transition temperature, the particles can be tailored to have controlled release properties. For example, by administering particles which include a phospholipid or combination of phospholipids which have a phase transition temperature higher than the patient's body temperature, the release of dopamine precursor, agonist or any combination of precursors and/or agonists can be slowed down. On the other hand, rapid release can be obtained by including in the particles phospholipids having lower transition temperatures. Particles having controlled release properties and methods of modulating release of a biologically active agent are described in U.S. Provisional Patent Application No. 60/150,742 entitled Modulation of Release From Dry Powder Formulations by Controlling Matrix Transition, filed on Aug. 25, 1999, the contents of which are incorporated herein in their entirety.

In another embodiment of the invention the particles can include a surfactant. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration.

In addition to lung surfactants, such as, for example, phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); and tyloxapol.

The surfactant can be present in the particles in an amount ranging from about 0 to about 90 weight %. Preferably, it can be present in the particles in an amount ranging from about 10 to about 60 weight %.

Methods of preparing and administering particles which are aerodynamically light and include surfactants, and, in particular phospholipids, are disclosed in U.S. Pat. No. 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety. Methods of administering particles to patients in acute distress are disclosed. The highly dispersible particles being administered in the instant invention are capable of being delivered to the lung and absorbed into the system when other conventional means of delivering drugs fail.

In yet another embodiment, highly dispersible particles only including a bioactive agent and surfactant are administered. Highly dispersible particles may be formed of the surfactant and include a therapeutic prophylactic, or diagnostic agent, to improve aerosolization efficiency due to reduced particle surface interactions, and to potentially reduce loss of the agent due to phagocytosis by alveolar macrophages.

In another embodiment of the invention, highly dispersible particles including an amino acid are administered. Hydrophobic amino acids are preferred. Suitable amino acids include naturally occurring and non-naturally occurring hydrophobic amino acids. Some naturally occurring hydrophobic amino acids, including but not limited to, non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1–C8 hydrocarbons which are completely saturated, which contain one or two heteroatoms such as nitrogen, oxygen or sulfur and/or which contain one or more units of desaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, —$NO_2$, —COOH, —$NH_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —$CONH_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—$NH_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acids analogs and salts thereof can be obtained commercially. Others can be synthesized by methods known in the art. Synthetic techniques are described, for example, in Green and Wuts, "*Protecting Groups in Organic Synthesis*", John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale, has a value greater or equal to 0.5, in other words, has a tendency to partition in the nonpolar acid which is at least equal to that of glycine.

Examples of amino acids which can be employed include, but are not limited to: glycine, proline, alanine, cysteine, methionine, valine, leucine, tyrosine, isoleucine, phenylalanine, tryptophan. Preferred hydrophobic amino acids include leucine, isoleucine, alanine, valine, phenylalanine and glycine. Combinations of hydrophobic amino acids can also be employed. Furthermore, combinations of hydrophobic and hydrophilic (preferentially partitioning in water) amino acids, where the overall combination is hydrophobic, can also be employed.

The amino acid can be present in the particles of the invention in an amount of at least 10 weight %. Preferably, the amino acid can be present in the particles in an amount ranging from about 20 to about 80 weight %. The salt of a hydrophobic amino acid can be present in the particles of the invention in an amount of at least 10 weight percent. Preferably, the amino acid salt is present in the particles in an amount ranging from about 20 to about 80 weight %. In preferred embodiments the particles have a tap density of less than about 0.4 g/cm$^3$.

Methods of forming and delivering particles which include an amino acid are described in U.S. patent application Ser. No. 09/382,959, filed on Aug. 25, 1999, entitled Use of Simple Amino Acids to Form Porous Particles During Spray Drying, the teachings of which are incorporated herein by reference in their entirety.

The particles of the invention can also include excipients such as one or more of the following; a sugar, such as lactose, a protein, such as albumin, cholesterol and/or a surfactant.

If the agent to be delivered is negatively charged (such as insulin), protamine or other positively charged molecules can be added to provide a lipophilic complex which results in the sustained release of the negatively charged agent. Negatively charged molecules can be used to render insoluble positively charged agents.

Highly dispersible particles suitable for use in the methods of the invention may be prepared using single and double emulsion solvent evaporation, spray drying, solvent extraction, solvent evaporation, phase separation, simple and complex coacervation, interfacial polymerization, supercritical carbon dioxide ($CO_2$) and other methods well known to those of ordinary skill in the art. Particles may be made using methods for making microspheres or microcapsules known in the art, provided that the conditions are optimized for forming particles with the desired aerodynamic diameter, or additional steps are performed to select particles with the density and diameter sufficient to provide the particles with an aerodynamic diameter between one and five microns, preferably between one and three microns.

With some polymeric systems, polymeric particles prepared using a single or double emulsion technique vary in size depending on the size of the droplets. If droplets in water-in-oil emulsions are not of a suitably small size to form particles with the desired size range, smaller droplets can be prepared, for example, by sonication or homogenization of the emulsion, or by the addition of surfactants.

If the particles prepared by any of the above methods have a size range outside of the desired range, particles can be sized, for example, using a sieve, and further separated according to density using techniques known to those of skill in the art.

The particles are preferably prepared by spray drying.

The following equipment and reagents are referred to herein and for convenience will be listed once with the pertinent information. Unless otherwise indicated, all equipment was used as directed in the manufacturer's instructions. Also, unless otherwise indicated, other similar equipment can be used as well know to those skilled in the art.

Unless otherwise indicated, all equipment and reagents were used as directed in the manufacturer's instructions. Further, unless otherwise indicated, that suitable substitution for said equipment and reagents would be available and well know to those skilled in the art.

(1) RODOS dry powder disperser (Sympatec Inc., Princeton, N.J.)
(2) HELOS laser diffractometer (Sympatec Inc., N.J.)
(3) Single-stage Andersen impactor (Andersen Inst., Sunyrna, Ga.)
(4) AeroDisperser (TSI, Inc., Amherst, Mass.)
(5) Aerosizer (TSI Inc., Amherst, Mass.)
(6) blister pack machine, Fantasy Blister Machine (Schaefer Tech, Inc., Indianapolis, Ind.)
(7) collapsed Andersen cascade impactor (consisting of stage 0 as defined by manufacturer) and the filter stage (Anderson Inst., Sunyra, Ga.)

(8) a spirometer (Spirometrics, USA, Auburn, Me.)
(9) a multistage liquid impinger (MSLI) (Erweka, USA, Milford, Conn.)
(10) fluorescent spectroscope (Hitachi Instruments, San Jose, Calif.)
(11) gamma camera (generic)

Reagents albuterol sulfate particles (Profarmco Inc., Italy)
human growth hormone (Eli Lilly, Indianapolis, Ind.)
size #2 methyl cellulose capsules (Shionogi, Japan)
blister packs (Heuck Foils, Well, N.J.)
DPPC (Avanti, Alabaster, Ala.)

As discussed in more detail in the Example section below, the methods of the instant invention require powders which exhibit good aerosolization properties from a simple inhaler device. In order to determine if a powder has the appropriate aerosolization properties, the powder is tested for deaggregation and emission properties. Although those skilled in the art will recognize equivalent means to measure these properties, an example of an in vitro test which demonstrates delivery of a mass of powder onto an impactor is performed. The powder to be tested is introduced into a powder dispensing apparatus, for example a RODOS dry powder disperser at varying shear forces. This is accomplished by manipulating the regulator pressure of the air stream used to break up the particles. The geometric size is measured to determine whether a powder has successfully deaggregated under the conditions. In addition to the deaggregation properties, it is possible to evaluate the ability of a powder to emit from a simple, breath-activated inhaler. Examples of inhalers suitable for the practice of the instant invention are the Spinhaler® (Fisons, Loughborough, U.K.), Rotahaler® (Glaxo-Wellcome, Research Triangle Park (RTP), North Carolina), FlowCaps® (Hovione, Loures, Portugal), Inhalator® (Boehringer-Ingelheim, Germany), and the Aerolizer® (Novartis, Switzerland). It will be appreciated that other inhalers such as the Diskhaler (Glaxo-Wellcome, RTP, N.C.) may also be used. Especially suitable inhalers are the simple, dry powder inhalers (U.S. Pat. Nos. 4,995,385 and 4,069, 819). A specific non-limiting example describing an experiment to determine the deaggregation and emission properties of three different powders is described in further detail herein. Briefly, three different dry powders believed to have different deaggregation properties were characterized. The first powder was micronized albuterol sulfate particles. The second and third powders were prepared by dissolving a combination of excipients and a bioactive agent in an ethanol/water solvent system and spray drying to create dry powders. The geometric diameter, tap density and aerodynamic diameter of the three powders were determined.

The Applicants introduced the powders into and dispersed the powder through an orifice in the RODOS dry powder disperser at varying shear forces by manipulating the regulator pressure of the air stream used to break up the particles. The Applicants obtained the geometric size distribution from the HELOS laser diffractometer as the powder exited and recorded the median value. The data was summarized and plotted as the mass median geometric diameter (MMGD) against pressure.

Applicants postulated and through experimentation disclosed herein found that at high pressure, for example 3 or 4 bars, all three powders exited the disperser as primary (deaggregated) particles. This supports the finding that relatively high energy successfully deaggregates all three powders. However at pressures below 2 bars which more closely corresponds with physiological breath rate, the micronized powder (Powder 1 Table 1) exited the orifice in an aggregated state, evidenced by a mean particle size leaving the orifice that was greater than the powder's primary particle size. This is not the case for the spray dried powders (Powder 2 and 3 Table 1), which emitted from the orifice at approximately their primary particles size. These powders are highly dispersible powders.

Still further to evaluate the ability of the three powders to emit from a simple, breath-activated inhaler, the Applicants placed 5 mg of each powder in a size #2 methyl cellulose capsule and inserted the capsule into a breath-activated inhaler. It will be appreciated by those skilled in the art that the receptacle into which the powders are placed will depend on the type of inhaler selected. The results are discussed in the Examples below. Generally, applicants found that given the relatively low energy supplied by the inhaler to break up the powder, the micronized albuterol sulfate powder were emitted from the inhaler as aggregates with geometric diameters greater than 30 microns, even thought their primary particle size, as measured by RODOS was on the order of 2 microns. On the other hand, the highly dispersible particles of spray dried albuterol sulfate of hGH were emitted at particle sizes that were very comparable to their primary particle size. The same results were obtained from measurements of the aerodynamic diameter, with spray dried particles emitting with very similar aerodynamic diameter as compared to the primary particles. Using the methods of the instant invention, one skilled in the art can achieve high-efficiency delivery from a simple breath-activated device by loading it with powder that is highly dispersible.

A further feature of the instant invention is the ability to emit large percentages of a nominal dose at low energy not only from single dose, breath-actuated inhaler but also from a range of breath-actuated Dry Powder Inhalers (DPIs).

To illustrate that a highly dispersible powder can efficiently emit and penetrate into the lungs from a range of breath-activated DPIs, the Applicants prepared a spray-dried powder comprised of sodium citrate, DPPC, calcium chloride buffer, and a rhodamine fluorescent label. This is explained thoroughly in Example 2. The powder possessed a median aerodynamic diameter of 2.1 $\mu$m (measured by the AeroDisperser and Aerosizer) and a geometric diameter of 11.0 $\mu$m (measured using the RODOS/HELOS combination described above). Applicants found that the powders tested displayed excellent deaggregation properties.

In particular, the Applicants placed 5 mg of the powders to be tested in the capsules using a semi-automated capsule filling device in the following inhalers: a breath activated inhaler under development by the applicant, the Spinhaler® (Fisons, Loughborough, U.K.), Rotahaler® (Glaxo-Wellcome, RTP, NC), FlowCaps® (Hovione, Loures, Portugal), Inhalator® (Boehringer-Ingelheim, Germany), and the Aerolizer® (Novartis, Switzerland). We also tested the Diskhaler (Glaxo-Wellcome, RTP, NC), for which 3 mg of the powder was machine-filled into the blister packs. Applicants connected each inhaler to a collapsed Andersen cascade impactor (consisting of stage 0 and the filter stage) and extracted air at 60 L/minute for 2 seconds after actuating the device. The fine particle fraction less than stage 0, having a 4.0 $\mu$m cut-off, was determined using fluorescent spectroscopy.

Applicants found that in each case, approximately 50% or more of the emitted dose displays a mean aerodynamic diameter (Da) less than 4 $\mu$m in size, indicating that the powder will efficiently enter the lungs of a human subject at a physiological breath rate, despite the simplicity of these breath-activated devices.

Figure 5:
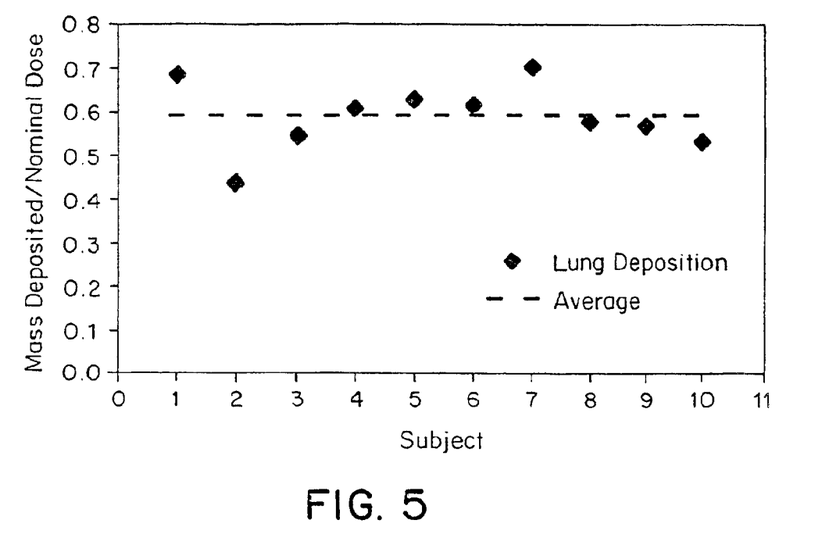
FIG. 5 is a graph showing the mass deposited in the lungs relative to the nominal dose (diamonds). The average deposition for the 10 individuals was 59% (dotted line).
Figure 6:
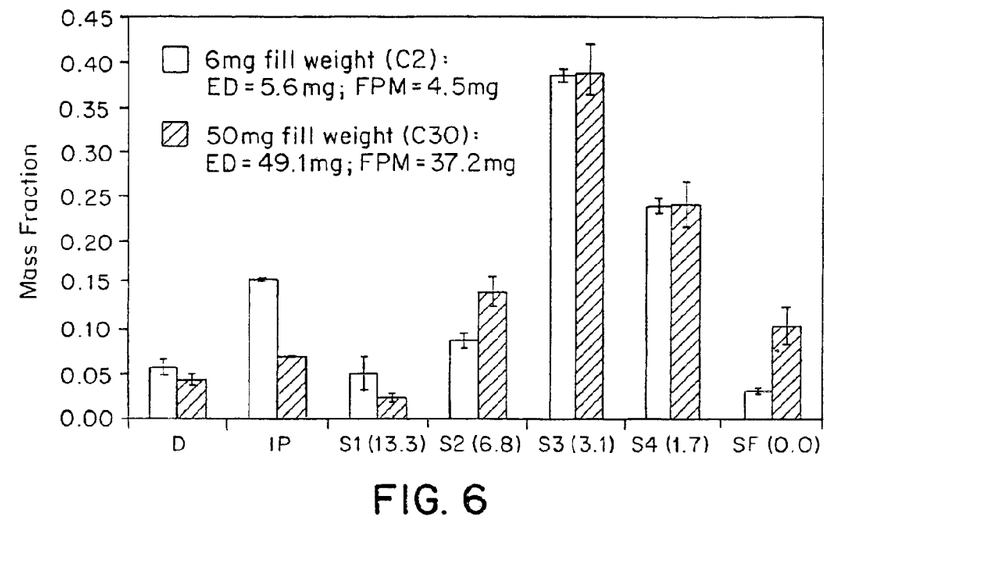
FIG. 6 is a bar graph showing a comparison of mass fraction distributions obtained for 6 (left bar) and 50 mg (right bar) fill weights.
Figure 7:
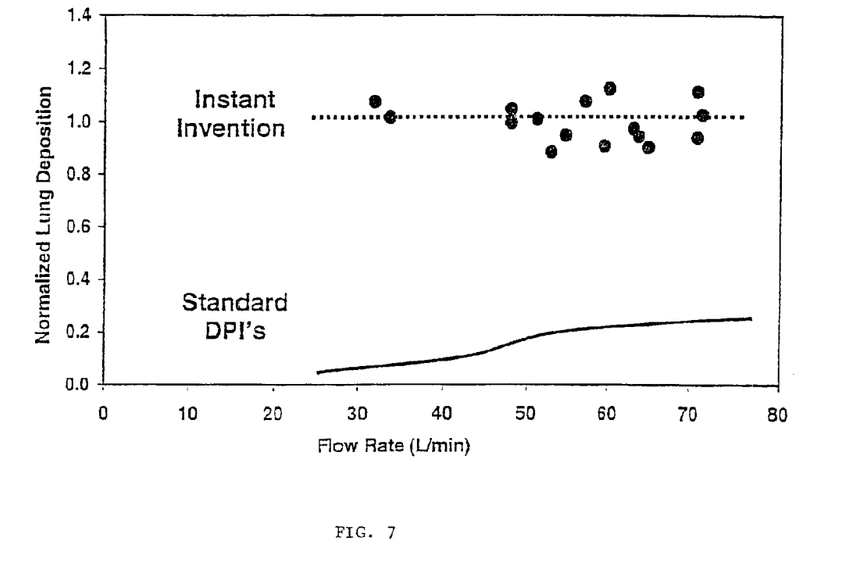
FIG. 7 is a graph showing the relative lung deposition of particles of the instant invention (circles) over a range of inspiratory flow rates in healthy volunteers. This is compared to lung deposition from dry powder inhalers (DPI's) (solid line) over the same range of inspiratory flow rates. For comparison to DPI's, deposition efficiency of the particles of the present invention were normalized to an average value of 1.0 (dotted line). The average efficiency of mass deposited in the lung divided by the nominal dose for particles of present invention is 59% as represented in FIG. 5.

In order to test the highly dispersible powders in vivo, Applicants performed human deposition studies as described in Example 3 to determine whether a highly dispersible powder emitted from a simple breath-actuated inhaler could produce highly efficient delivery to the lungs (>50% of the nominal dose). This is especially important because many devices rely on inhalation by the patient to provide the power to break up the dry material int a free-flowing powder. Such devices prove ineffective for those lacking the capacity to strongly inhale, such as young patients, old patients, infirm patients, or patients with asthma or other breathing difficulties. An advantage of the method of the instant invention is that highly efficient delivery can be achieved independent of the flow rate. Thus, using the methods of the invention, even a weak inhalation is sufficient to delivery the desired dose. This is surprising in light of the expected capabilities of standard DPIs. As can be seen in FIG. 7 using the methods herein superior delivery compared to standard DPIs can be achieved at flow rates ranging from about 25 L/min to about 75 L/min. The methods of the instant invention can be optimized at flow rates of at least about 20 L/min to about 90 L/min. Powder possessing the following characteristics Dg=6.7 $\mu$m; p=0.06 g/cc; Da=1.6 $\mu$m was labeled with $^{99m}$Tc nanoparticles. Equivalence between the mass and gamma radiation particle size distributions was obtained and is discussed in detail in Example 3 below. Approximately 5 mg of powder was loaded into size 2 capsules. The capsules were placed into a breath activated inhaler and actuated. Ten healthy subjects inhaled through the inhaler at an approximately inspiratory flow rate of 60 L/min. as measured by a spirometer. The deposition image was obtained using a gamma camera. The percentage lung deposition (relative to the nominal dose) obtained from the ten subjects is shown in FIG. 5. The average lung deposition relative to the nominal dose was 59.0%. Those skilled in the art would recognize that such deposition levels confirm that highly dispersible drug powder can be inhaled into the lungs with high efficiency using a single breath-actuated inhaler.

Still further, Applicants have discovered that the same preparations of a highly dispersible powder that had excellent aerosolization from a single inhaler can be used to deliver a surprisingly high dose in single inhalation. The highly dispersible powder can be loaded into a large pre-metered dose (50 mg) and a smaller pre-metered dose (6 mg). The particle characteristics of the powder were as follows: Dg=10.6 $\mu$m; p=0.11 g/cc; Da=3.5 $\mu$m. One skilled in the art would appreciate the possible ranges of characteristics of particles suitable for use in the instant invention as disclosed previously herein.

The aerodynamic particle size distributions were characterized using a multistage liquid impinger (MSLI) [ ] operated at 60 L/min. Size 2 capsules were used for the 6 mg dose and size 000 capsules were used for the 50 mg dose. The Applicants compared the two particle size distributions obtained for the 6 and 50 mg doses. The fine particle fraction <6.8 $\mu$m relative to the total dose (FPF$_{TD}$<6.8 $\mu$m) for the 6 and 50 mg doses were 74.4% and 75.0%, respectively. Thus Applicants have demonstrated that a large dose of drug can be delivered to the lungs with equal efficiency as a small drug dose by combining the properties of a highly dispersible powder.

EXEMPLIFICATION

Unless otherwise noted, the apparatus and reagents used have been obtained from the sources previously listed herein.

Example 1

The powders suitable for use in the methods of the instant invention are required to possess properties which exhibit good aerosolization from a simple inhaler device. To determine the properties, Applicants characterized three different dry powders believed to have different deaggregation properties. The first powder to be tested was micronized albuterol sulfate particles obtained from Spectrum Labs. The second and third powders were prepared by spray-drying by dissolving a combination of excipients and a bioactive agent in an ethanol/water solvent system.

Preparation of Microparticles

Placebo particle composition is 70/20/10% DPPC/sodium citrate/Calcium chloride 0.2 grams sodium citrate and 0.1 grams calcium chloride were dissolved in 0.11 liters water. A DPPC solution in ethanol was prepared by dissolving 0.7 g DPPC (DL-$\alpha$-phosphatidylcholine dipalmitoyl, Avanti Polar Lipids, Alabaster, Ala.) in 0.89 liters of 95% ethanol. The sodium citrate/calcium chloride solution and the DPPC/ethanol solution were then mixed together. The final total solute concentration is 1.0 g/L made up of 0.70 g/L DPPC, 0.2 g/L sodium citrate and 0.1 g/L calcium chloride in 85% ethanol/15% water.

hGH particle composition is: 58/38.5/3.5 hGH/DPPC/Sodium Phosphate 1.16 gr hGH (Lilly, Indianapolis, Ind.) was dissolved in 300 ml sodium phosphate buffer (10 mM, Ph 7.4). 0.77 g DPPC was dissolved in 700 ml ethanol. The two solutions were then combined resulting in a final solute concentration of 2 g/L in 70/30 EtOH/H$_2$O.

Albuterol sulfate particle composition is 76/20/4 DSPC/Leucine/Albuterol Sulfate 2.28 g DSPC (disteoroyl phosphatidylcholine, Avanti Polar Labs) and 0.6 g Leucine (Spectrum Labs, Laguna Hills, Calif.) were dissolved in 700 ml. ethanol. 0.12 g albuterol sulfate (Profarmco, Italy) was dissolved in 300 ml water and then the two solutions were combined to yield a final solute concentration of 3 g/L in 70/30 EtOH/H$_2$O.

Spray Drying

A Niro Atomizer Portable Spray Dryer (Niro, Inc., Columbus, Md.) was used to produce the dry powders. Compressed air with variable pressure (1 to 5 bar) ran a rotary atomizer (2,000 to 30,000 rpm) located above the dryer. Liquid feed with varying rate (20 to 66 ml/min) was pumped continuously by an electronic metering pump (LMI, model #A151-192s) to the atomizer. Both the inlet and outlet temperatures were measured. The inlet temperature was controlled manually; it could be varied between 100° C. and 400° C. and was established at 100, 110, 150, 175, or 200° C., with a limit of control of 5° C. The outlet temperature was determined was determined by the inlet temperature and such factors as the gas and liquid feed rates: it varied between 50° C. and 130° C. A container was tightly attached to the cyclone for collecting the powder product.

Results

The geometric diameter and tap density of the three powders are shown in Table

TABLE 1

| Powder | Dg ($\mu$m) | $\rho$ (g/cc) |
|---|---|---|
| Micronized Alb. Sulfate (1) | 2.5 | 0.26 |
| Spray-Dried Alb. Sulfate (2) | 8.0 | 0.20 |
| Spray-Dried hGH (3) | 14.5 | 0.07 |

Figure 1:
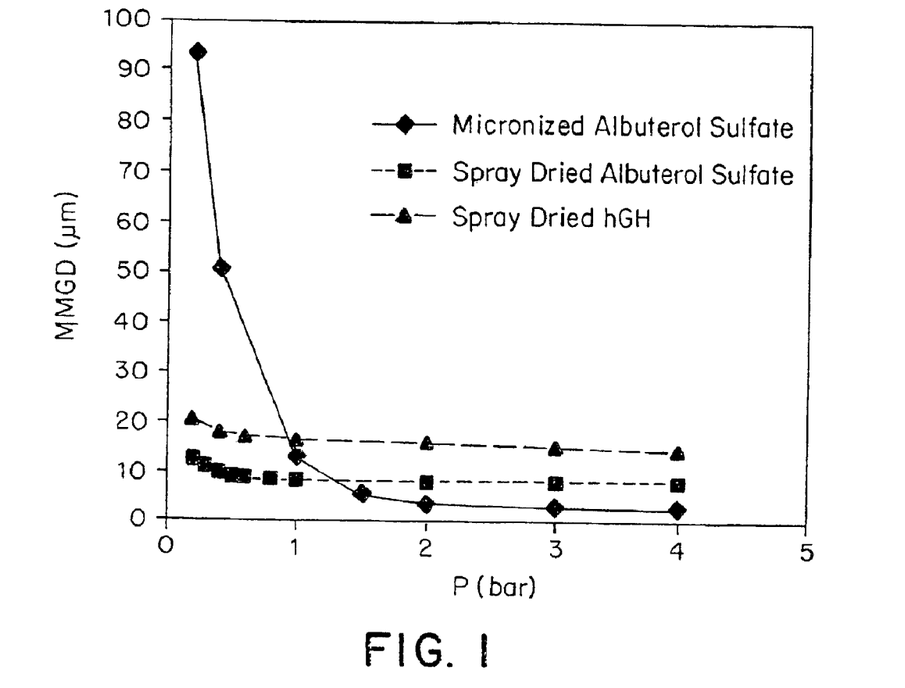
FIG. 1 is a graph showing mass median geometric diameter (MMGD) in microns plotted against pressure for micronized albuterol sulfate (diamonds), spray dried albuterol sulfate (squares) and spray dried hGH (triangles).

To evaluate the deagglomeration properties of the three powders, Applicants introduced the powders into the RODOS dry powder disperser at varying shear forces by manipulating the regulator pressure of the air stream used to break up the particles. Subsequently, following the manufacturer's instructions, Applicants obtained the geometric size distribution from the HELOS laser diffractometer and recorded the median value. The data was summarized and plotted as volume median geometric diameter (MMGD) against pressure.

FIG. 1 shows the results of this experiment. Applicants have demonstrated that at high pressure, about greater than 2 bars and especially about 3 to 4 bars, all three powders exit the disperser as primary (deaggregated) particles. This supports the finding that a relatively high energy successfully deaggregates all three powders. However at pressures below 2 bars, the micronized powder [Powder 1] exited the orifice in an aggregated state. Evidence of this can be seen by a mean particle size leaving the orifice that was greater than the powders primary particle size. This was not the case for the spray dried powders [Powders 2 and 3], which emitted from the orifice at approximately their primary particles' size. Powders 2 and 3 were highly dispersible powders.

Particles of the present invention were further characterized by the following techniques. The primary geometric diameter was measured using a RODOS dry powder disperser (Sympatec, Princeton, N.J.) in conjunction with a HELOS laser diffractometer (Sympatec). Powder was introduced into the RODOS inlet and aerosolized by shear forces generated by a compressed air stream regulated at 4 bar. The aerosol cloud was subsequently drawn into the measuring zone of the HELOS, where it scattered light from a laser beam and produced a Fraunhofer diffraction pattern used to infer the particle size distribution.

The geometric diameter emitted from the breath activated inhaler was measured using an IHA accessory (Sympatec) with the HELOS laser diffractometer. The IHA adapter positions the DPI in front of the measuring zone and allows air to be pulled through the DPI to aerosolize the powder. Vacuum was drawn at 30 L/min to disperse powder from the AIR inhaler and the geometric diameter was measured by Fraunhofer diffraction.

The primary aerodynamic diameter was measured using an AeroDisperser/Aerosizer (TSI Inc., Amherst, Mass.). The sample powder was aerosolized by an inlet air stream at 1 psi in the AeroDisperser and then accelerated to sonic velocity into the Aerosizer. The Aerosizer measures the time taken for each particle to pass between two fixed laser beams, which is dependent on the particle's inertia. The TOF measurements were subsequently converted into aerodynamic diameters using Stokes law.

The emitted aerodynamic diameter from the AIR inhaler was determined using the AeroBreather (TSI Inc., Amherst, Mass.) in conjunction with the Aerosizer (TSI, Inc.) The powder was aerosolized from the inhaler at 30 L/min into the AeroBreather chamber and allowed to settle into the Aerosizer.

Figure 2A:
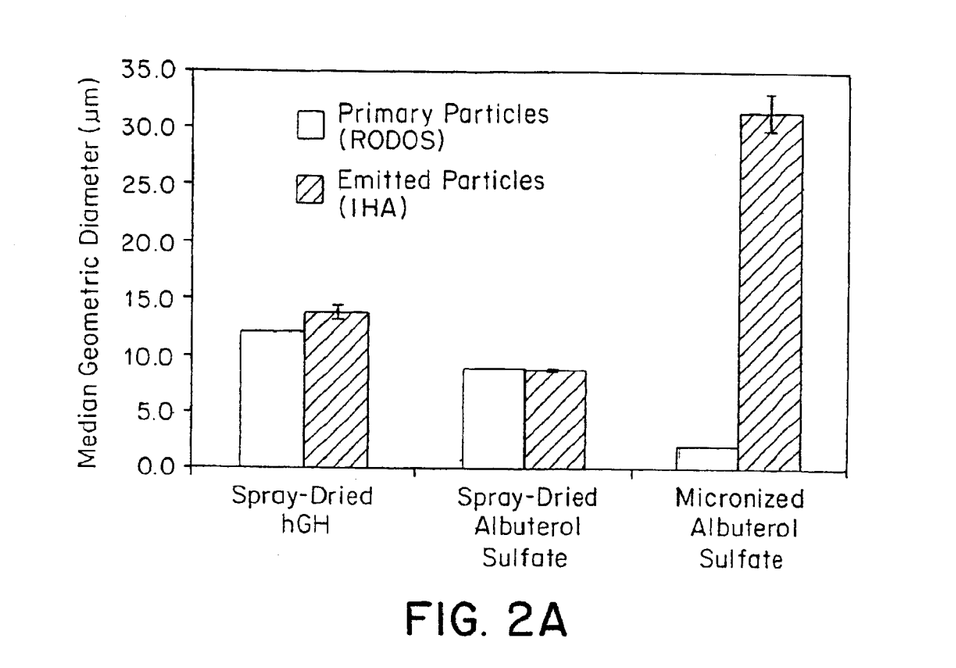
FIG. 2A is a bar graph showing median geometric diameter of micronized albuterol sulfate, spray dried albuterol sulfate and spray dried hGH as primary particles (left bar of each pair), as measured by RODOS, compared to emitted particles (right bar of each pair) out of the inhaler at 30 L/min, as measured by IHA.
Figure 2B:
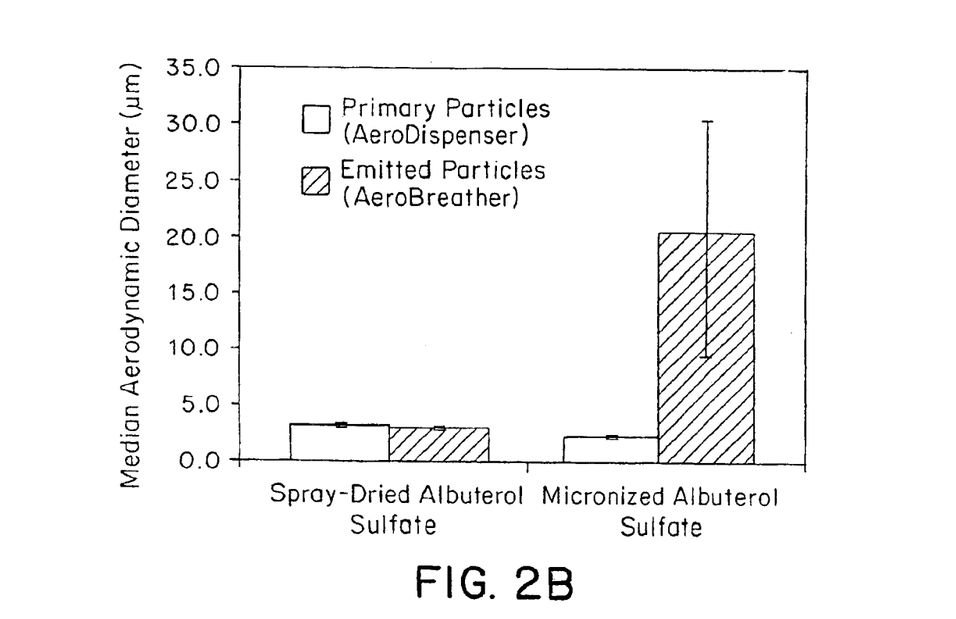
FIG. 2B is a bar graph showing median aerodynamic diameter of micronized albuterol sulfate and spray dried albuterol sulfate as primary particles (left bar), as measured by a AeroDispenser, compared to emitted particles (right bar) out of the inhaler at 30 L/min, as measured by Aero-Breather.

Using these techniques, the inventors compared the primary size from the dry powder disperser at 4 bar to the emitted size from the AIR inhaler at 30 L/min (FIG. 2A). As can be seen, the spray dried hGH and spray dried albuterol sulfate emitted particle size was almost identical to their measured primary particle size, which is not the case for the micronized albuterol sulfate. Finally, the inventors also measured primary and emitted aerodynamic size for the spray dried albuterol sulfate and compared it to the micronized albuterol sulfate (FIG. 2B). Again, the spray dried albuterol sulfate emitted with a nearly identical aerodynamic diameter as its primary particles aerodynamic diameter while the micronized albuterol sulfate emitted with a much larger aerodynamic diameter than its primary particles aerodynamic diameter. This further confirms that the spray dried powders of the present invention disperse into respirable particles while the micronized drug remains nonrespirable even though its primary size is respirable.

The results of this example demonstrate that using the methods of the instant invention, Applicants achieved high-efficiency delivery from a simple breath-activated device by loading it with powder that is highly dispersible.

Example 2

To illustrate that a highly dispersing powder can efficiently emit and penetrate into the lungs from a range of breath-activated dry powder inhalers (DPIs), Applicants prepared a spray-dried powder comprised of sodium citrate, DPPC, calcium chloride buffer, and a trace amount of a rhodamine fluorescent label. The powder possessed a median aerodynamic diameter of 2.1 $\mu$m (measured by the AeroDisperser and Aerosizer) and a geometric diameter of 11.0 $\mu$m (measured using the RODOS/HELOS) and displayed excellent deaggregation properties similar to the spray-dried powders in Example 1.

Figure 3:
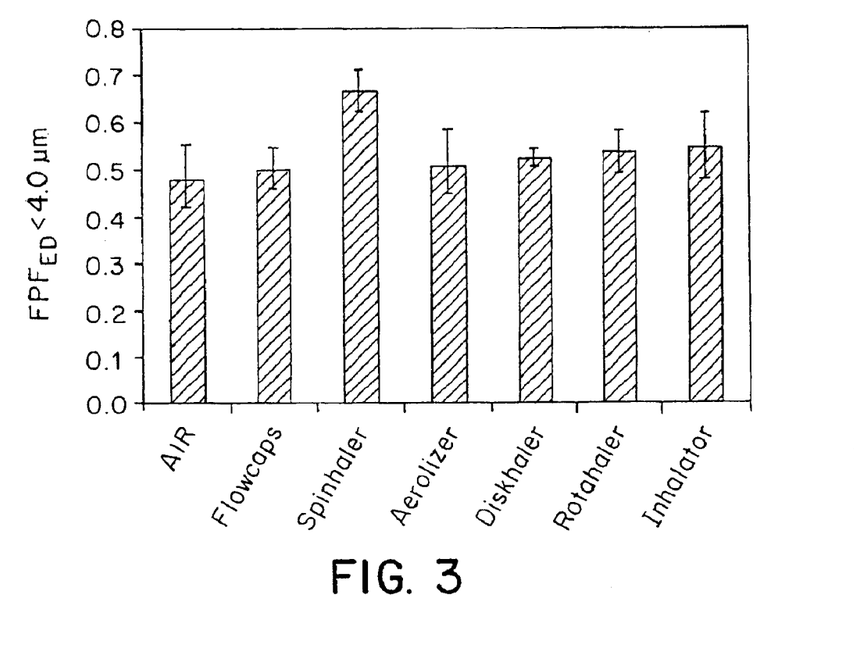
FIG. 3 is a bar graph showing the Fine Particle Fraction (FPF)>4.0 microns of the Emitted Dose Using DPI's at 60 L/min.
Figure 4:
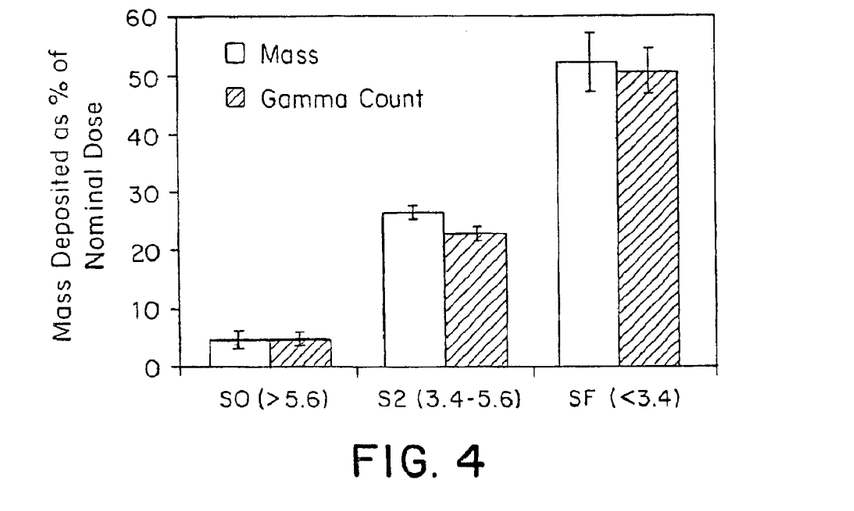
FIG. 4 is a bar graph showing a comparison of mass (left bar) and gamma count (right bar) particle size distributions of radio labeled particles.

Applicants placed 5 mg of the powder in the capsules using a semi-automated capsule filling device in the following inhalers: a breath activated inhaler under development by the applicant AIR Inhaler, the Spinhaler® (Fisons, Loughborough, U.K.), Rotahaler® (Glaxo-Wellcome, RTP, NC), FlowCaps® (Hovione, Loures, Portugal), Inhalator® (Boehringer-Ingelheim, Germany), and the Aerolizer® (Novartis, Switzerland). Applicants also tested the Diskhaler (Glaxo-Wellcome, RTP, NC), for which 3 mg of the powder was machine-filled into the blister packs. Applicants connected each inhaler to a collapsed Andersen cascade impactor (consisting of stage 0 and the filter stage) and extracted air at 60 L/minutes for 2 seconds after actuating the device. The fine particle fraction less than stage 0, having a 4.0 $\mu$m cut-off, was determined using fluorescent spectroscopy.

FIG. 3 shows the results from the study. Applicants found that in each case, approximately 50% or more of the emitted dose displays a mean aerodynamic diameter (Da) less than 4 $\mu$m in size, indicating that the powder efficiently would enter the lungs of a human subject at a physiological breath rate, despite the simplicity of these breath-activated devices. Applicants also demonstrated that using the methods of the instant invention, large percentages of a nominal dose at low energy were emitted from not only single dose, breath-actuated inhalers but also from a range of breath-actuated dry powder inhalers (DPIs).

Example 3

A human deposition study was performed to determine whether a highly dispersible powder emitted from a simple breath-actuated inhaler could produce highly efficient delivery to the lungs (>50% of the nominal dose). Powders possessing the following characteristics were used: Dg=6.7 $\mu$m; $\rho$=0.06 g/cc; Da=1.6 $\mu$m.

The powder was labeled with $^{99m}$Tc nanoparticles.

Human Deposition Studies

Gamma scintigraphy is an established methodology for assessing the pattern of deposition of inhaled particles. In this example the test substance is labelled with a small dose of the radioisotope $^{99m}$Tc at the InAMed laboratories (Gauting, Germany). Determination of the lung border is enhanced by undertaking an $^{81m}$Kr ventilation scan. Inspiratory flow rates were monitored to ensure that a deep, comfortable inhalation has been performed during the depo- 
sition study. The range of peak inspiratory flow rates (PIFR) for a deep comfortable inhalation through the breath activated inhaler was assessed prior to study start. PIFRs outside the specified range will be repeated.

Studies were performed in 10 normal subjects A baseline ventilation scan was undertaken to assist definition of the lung borders. Lung function was assessed before and after each test inhalation. Deposition was determined following inhalation by gamma scintigraphy. Inspiratory flow rates through a breath activated inhaler were monitored during the deposition using a spirometer.

Subjects were trained to inhale through a breath activated inhaler with a deep, comfortable inhalation. Subjects were trained to achieve a peak inspiratory flow rate (PIFR) through a breath activated inhaler within a specified range representing a deep, comfortable inhalation. The breath activated inhaler was actuated and attached to the spirometer to monitor the inspiratory flow rate during the deposition study. The subject took a capsule from the appropriate box, according to the predetermined randomisation schedule, and placed it in the inhaler/spirometer device immediately prior to use.

Each subject was relaxed and breathing normally (for at least 5 breaths). The inhaler mouthpiece is placed in the mouth at the end of a normal exhalation. The subject inhaled through the mouth with a deep, comfortable inhalation until the lungs are full. The subject then held their breath for approximately 5 seconds (by counting slowly to 5). Deposition was measured in the gamma camera immediately after exhalation. A further lung function test was then performed using a Jaeger body plethysmograph, (Jaeger, Würzburg, Germany).

Materials and Methods

The placebo powder, comprised of 70/20/10% w/w DPPC/Sodium Citrate/Calcium Chloride, which was used had the following characteristics: Dg=6.7 um; $\rho$=0.06 g/cc; Da=1.6 um. The primary aerodynamic particle size characteristics were obtained using time-of-flight (AeroSizer/AeroDisperser) and the geometric particle size characteristics using laser diffraction (RODOS/HELOS) operated at 1 and 2 bar. Emitted aerodynamic particle size characteristics were obtained using Andersen cascade impaction (gravimetric analysis) operated at 28.3 L/min, for a total air volume of 2 L. Geometric particle size characteristics were obtained using laser diffraction (IHA/HELOS, Sympatec, NJ) operated at 60 L/min.

Powder Radiolabeling

Placebo powder was filled in a reservoir which was closed by an 0.2 $\mu$m filter. A $^{99m}$Tc solution (0.5 ml $^{99m}$Tc in isotonic saline added to 100 ml of deionized water) was filled in a Pari Jet nebulizer which was placed in a drying chamber. The Pari Jet nebulizer was activated for 3 min to nebulize 1.5 ml of the $^{99m}$Tc solution. The particles were dried in this chamber and lead through the reservoir containing the powder. The humidity in the labelling chamber was controlled and never exceeded 30% relative humidity.

Because of the short half life of the $^{99m}$Tc, the labelling was performed 2–4 hours before the inhalation. The activity of the powder was corrected for the physical decay of the Technetium, to get the actual activity which was available at the beginning of the inhalation.

The emitted aerodynamic particle size distribution of the post-labeled powder was obtained using an 8-stage Andersen cascade impactor (gravimetric analysis) to verify that the radiolabeling process did not affect the particle size distribution.

Size 2 capsules were hand filled with 5(±1) mg of the radiolabeled powder. Each capsule was numbered and its filled weight and level of radioactivity were recorded. The subject took a capsule and placed it in the inhaler/spirometer device immediately prior to use.

Methodology for the Determination of Powder in the Regions of the Lung

The inhalation of the labelled porous particles was performed while the subject was sitting with his back against the gamma camera. After inhalation a gamma scintigraphic image was taken while the subject was sitting upright with their back in front of the camera. The inhalation time and breath holding period was recorded. The size of the lungs was determined by an $^{81}$Kr scan. This radioactive gas was inhaled by the subject before or at the end of the study.

From the Krypton ventilation scan of the subject the outline of the lungs was taken. Because the subject was sitting in the same position at the Krypton scan and the powder inhalation there were 4 regions of interest (ROI) that were defined: left lung, right lung, stomach and oropharynx (including upper part of trachea).

These 4 ROIs were copied to the gamma camera image of the powder inhalation. In a region outside of the subject's lung, the background activity was defined and subtracted pixel by pixel from the entire image. Then the number of counts was determined for the 4 ROIs. These numbers were corrected by an attenuation factor for the single regions. After this correction the relative amount of intrathoracic versus extrathoracic particle deposition was determined.

Equivalence between the mass and gamma radiation particle size distributions was obtained, as shown in FIG. 4. Approximately 5 mg of powder was loaded into size 2 capsules. The capsules were placed into a breath activated inhaler under development by the applicant (AIR inhaler) and then the inhaler was actuated. Ten healthy subjects inhaled through the inhaler at an approximately inspiratory flow rate of 60 L/min. (The actual inspiratory flow rate varied from subject to subject over a range of 20 to 90 L/min., consistent with the normal range of inspiratory flow rates in humans). 60 L/min is a good average flow rate and is what is used experimentally to mimic inspiratory flow. As measured by a spirometer, the deposition image was obtained using a gamma camera. The percentage lung deposition (relative to the nominal dose) obtained from the ten subjects is shown in FIG. 5. The average lung deposition relative to the nominal dose was 59.0%.

Through this experiment, the Applicants confirmed that highly dispersible powder comprising drug can be inhaled into the lungs with high efficiency using a simple breath-actuated inhaler.

Example 4

To demonstrate that the same preparations of a highly dispersing powder that had excellent aersolization properties from a simple inhaler can be used to deliver a surprisingly high dose in single inhalation, Applicants prepared a highly dispersible powder and loaded the powder to obtain a large pre-metered dose (50 mg) and a smaller pre-metered dose (6 mg). The particle size characteristics of the powder were as follows:Dg=10.6 μm; ρ=0.11 g/cc; Da=3.5 μm.

The aerodynamic particle size distributions were characterized using a multistage liquid impinger (MSLI) operated at 60 L/min. Size 2 capsules were used for the 6 mg dose and size 000 capsules were used for the 50 mg dose. FIG. 6 shows the results comparing the two particle size distributions obtained for the 6 and 50 mg doses. The fine particle fraction <6.8 μm relative to the total dose ($FPF_{TD}$<6.8 μm) for the 6 and 50 mg doses were 74.4% and 75.0%, respectively.

This experiment demonstrated that a surprisingly large dose of drug can be delivered to the lungs with equal efficiency as a small drug dose by combining the properties of a highly dispersible powder with the methods of the instant invention.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of delivering a therapeutic dose of a bioactive agent to the pulmonary system of a subject, in a single, breath-activated step, comprising:

administering particles comprising a bioactive agent, from a receptacle having a mass consisting of said particles, to a subject's respiratory tract, wherein:

i) the particles administered to the subject's respiratory tract have a tap density of less than 0.4 g/cm$^3$;

ii) at least 50% of the particles have a fine particle fraction less than 4.0 μm; and iii) at least about 50% of the mass of particles stored in the receptacle is delivered to the pulmonary system of the subject.

2. The method of claim 1 wherein the particles have a tap density of less than about 0.1% g/cm$^3$.

3. The method of claim 1 wherein the particles have a geometric diameter greater than about 5 μm.

4. The method of claim 1 wherein the receptacle has a volume of at least about 0.37 cm$^3$.

5. The method of claim 1 wherein the receptacle has a volume of at least about 0.48 cm$^3$.

6. The method of claim 1 wherein the receptacle has a volume of at least about 0.67 cm$^3$.

7. The method of claim 1 wherein the receptacle has a volume of at least about 0.95 cm$^3$.

8. The method of claim 1 wherein delivery is primarily to the deep lung.

9. The method of claim 1 wherein delivery is primarily to the central airways.

10. The method of claim 1 wherein the bioactive agent is albuterol sulfate.

11. The method of claim 1 wherein the bioactive agent is insulin.

12. The method of claim 1 wherein the bioactive agent is growth hormone.

13. The method of claim 1 wherein the bioactive agent is fluticasone.

14. The method of claim 1 wherein the bioactive agent is salmeterol.

15. The method of claim 1 wherein the bioactive agent is hydrophobic drug.

16. The method of claim 1 wherein the bioactive agent is a hydrophilic drug.

17. The method of claim 1 wherein the bioactive agent is a monoclonal antibody.

18. The method of claim 1 wherein the particles are in the form of a dry powder.

19. The method of claim 1 wherein administration to the respiratory tract is by a dry powder inhaler.

* * * * *